United States Patent [19]
Rohr et al.

[11] 3,960,919
[45] June 1, 1976

[54] SUBSTITUTED SULFONYLGLYCOLIC ACID ANILIDES

[75] Inventors: Wolfgang Rohr, Mannheim; Adolf Fischer, Mutterstadt, both of Germany

[73] Assignee: Badische Anilin- & Soda-Fabrik Aktiengesellschaft, Ludwigshafen (Rhine), Germany

[22] Filed: Oct. 7, 1974

[21] Appl. No.: 512,670

Related U.S. Application Data

[62] Division of Ser. No. 310,640, Nov. 29, 1972, Pat. No. 3,865,860.

[30] Foreign Application Priority Data

Dec. 6, 1971    Germany ...................... 2160380

[52] U.S. Cl. ............................................ 260/456 A
[51] Int. Cl.² ........................................ C07C 143/38

[58] Field of Search .................... 260/456 A, 456 P

[56]       References Cited
         UNITED STATES PATENTS

| | | | |
|---|---|---|---|
| 3,536,721 | 10/1970 | Soong et al. | 260/456 A |
| 3,687,998 | 8/1972 | Trepka | 260/456 A |

*Primary Examiner*—James O. Thomas, Jr.
*Assistant Examiner*—Nicky Chan
*Attorney, Agent, or Firm*—Johnston, Keil, Thompson & Shurtleff

[57]            ABSTRACT

New and valuable N-substituted sulfonylglycolic acid anilides and a process for controlling the growth of unwanted plants with these compounds.

6 Claims, No Drawings

SUBSTITUTED SULFONYLGLYCOLIC ACID ANILIDES

This is a division of application Ser. No. 310,640 filed Nov. 29, 1972, now U.S. Pat. No. 3,865,860.

The present invention relates to new and valuable N-substituted sulfonylglycolic acid anilides and their use as herbicides.

It is known to use substituted acid anilides, e.g., chloroacetic acid-N-isopropylanilide, chloroacetic acid-N-propargylanilide and chloroacetic acid-N-isobutynylanilide as herbicides. However, their action is unsatisfactory.

We have now found that N-substituted sulfonylglycolic acid anilides of the formula

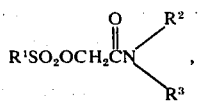

where R¹ denotes alkyl, cycloalkyl, haloalkyl, aralkyl, alkenyl, or haloalkenyl, or phenyl which may be substituted by alkyl, haloalkyl, alkoxy, halogen or nitro, R² denotes phenyl which may be substituted by alkyl, and R³ denotes alkyl of more than 2 carbon atoms, cycloalkyl, alkenyl or alkynyl, have a good herbicidal action.

R¹ may for instance have the following meanings: methyl, chloromethyl, ethyl, 2-chloroethyl, n-propyl, isopropyl, n-butyl, isobutyl, sec-butyl, tert-butyl, pentyl, cyclopentyl, hexyl, cyclohexyl, benzyl, vinyl, allyl, butenyl, pentenyl, hexenyl, phenyl, 4-methylphenyl, 4-chlorophenyl, 4-bromophenyl, 4-nitrophenyl, 4-fluorophenyl, 4-iodophenyl, 4-ethylphenyl, 2-nitrophenyl, 3-nitrophenyl, 3,4-dichlorophenyl, etc.

R² may for instance have the following meanings: phenyl, 2-methylphenyl, 3-methylphenyl, 4-methylphenyl, 2-ethylphenyl, 4-ethylphenyl, 2,6-dimethylphenyl, 2,6-diethylphenyl, 2,5-dimethylphenyl, 3,5-dimethylphenyl, 3,4-dimethylphenyl, 2,4-dimethylphenyl, 2,3-dimethylphenyl, 2,4,6-trimethylphenyl, 2,4,5-trimethylphenyl, 4-isopropylphenyl, 2-isopropylphenyl, 2-methyl-6-ethylphenyl, 2,6-diisopropylphenyl, etc.

R³ may for instance denote the following radicals: n-propyl, isopropyl, n-butyl, isobutyl, sec-butyl, tert-butyl, pentyl, cyclopentyl, hexyl, cyclohexyl, allyl, butenyl, pentenyl, hexenyl, propargyl, butynyl, pentynyl and hexynyl.

The compounds of the invention may be prepared by reacting a substituted glycolic acid anilide with a substituted sulfonyl chloride in the presence of an acid acceptor such as triethylamine.

The preparation of the compounds of the invention is illustrated in the following examples.

EXAMPLE 1

Preparation of O-methylsulfonylglycolic acid-(N-butyn-1-yl-3)-anilide

At 0°C and over a period of 20 minutes, a solution of 21 parts by weight of methanesulfochloride in 26 parts by weight of dichloromethane was added to a solution of 30.5 parts by weight of N-butyn-1-yl-3-glycolic acid anilide and 27.6 parts of triethylamine in 920 parts by weight of dichloromethane. After 45 minutes the reaction mixture was washed with ice water, with cold 5% hydrochloric acid and subsequently with cold saturated sodium bicarbonate solution. The organic phase was dried with magnesium sulfate and concentrated in vacuo. During cooling the oily residue crystallized upon a small amount of ether being added. The crude product was recrystallized from ether; melting point: 58° to 60°C.

The compound has the following structural formula:

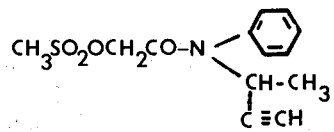

The following compounds for instance may be prepared analogously:

O-methylsulfonylglycolic acid-(N-propargyl)-anilide
O-ethylsulfonylglycolic acid-(N-propargyl)-anilide
O-propylsulfonylglycolic acid-(N-propargyl)-anilide
O-isopropylsulfonylglycolic acid-(N-propargyl)-anilide
O-n-butylsulfonylglycolic acid-(N-propargyl)-anilide
O-ethylsulfonylglycolic acid-(N-butyn-1-yl-3)-anilide, m.p. 76° to 78°C
O-propylsulfonylglycolic acid-(N-butyn-1-yl-3)-anilide, m.p. 50° to 52°C
O-isopropylsulfonylglycolic acid-(N-butyn-1-yl-3)-anilide, m.p. 83° to 85°C
O-n-butylsulfonylglycolic acid-(N-butyn-1-yl-3)-anilide, m.p. 69° to 71°C
O-cyclohexylsulfonylglycolic acid-(N-butyn-1-yl-3)-anilide, m.p. 99° to 100°C
O-chloromethylsulfonylglycolic acid-(N-butyn-1-yl-3)-anilide, m.p. 80° to 81°C
O-methylsulfonylglycolic acid-(N-3-methylbutyn-1-yl-3)-anilide, m.p. 89° to 90°C
O-ethylsulfonylglycolic acid-(N-3-methylbutyn-1-yl-3)-anilide
O-propylsulfonylglycolic acid-(N-3-methylbutyn-1-yl-3)-anilide
O-isopropylsulfonylglycolic acid-(N-3-methylbutyn-1-yl-3)-anilide
O-n-butylsulfonylglycolic acid-(N-3-methylbutyn-1-yl-3)-anilide
O-phenylsulfonylglycolic acid-(N-butyn-1-yl-3)-anilide, m.p. 86° to 87°C
O-4-methylphenylsulfonylglycolic acid-(N-butyn-1-yl-3)-anilide, m.p. 67° to 69°C
O-4-chlorophenylsulfonylglycolic acid-(N-butyn-1-yl-3)-anilide, oil
O-methylsulfonylglycolic acid-(N-isopropyl)-anilide, m.p. 92° to 93°C
O-methylsulfonylglycolic acid-(N-isobutyl)-anilide, m.p. 70° to 71°C
O-methylsulfonylglycolic acid-(N-tert-butyl)-anilide
O-ethylsulfonylglycolic acid-(N-isopropyl)-anilide, m.p. 60° to 61°C
O-ethylsulfonylglycolic acid-(N-isobutyl)-anilide
O-ethylsulfonylglycolic acid-(N-tert-butyl)-anilide
O-propylsulfonylglycolic acid-(N-isopropyl)-anilide, m.p. 56° to 57°C
O-propylsulfonylglycolic acid-(N-isobutyl)-anilide
O-isopropylsulfonylglycolic acid-(N-isopropyl)-anilide, m.p. 60° to 62°C
O-phenylsulfonylglycolic acid-(N-isopropyl)-anilide O-4-methylphenylsulfonylglycolic acid-(N-isopropyl)-anilide
O-4-chlorophenylsulfonylglycolic acid-(N-isopropyl)-anilide
O-phenylsulfonylglycolic acid-(N-propargyl)-anilide
O-4-methylphenylsulfonylglycolic acid-(N-propargyl)-anilide
O-4-chlorophenylsulfonylglycolic acid-(N-propargyl)-anilide
O-methylsulfonylglycolic acid-(N-allyl)-anilide
O-ethylsulfonylglycolic acid-(N-allyl)-anilide
O-propylsulfonylglycolic acid-(N-allyl)-anilide
O-n-butylsulfonylglycolic acid-(N-allyl)-anilide
O-phenylsulfonylglycolic acid-(N-allyl)-anilide
O-4-methylphenylsulfonylglycolic acid-(N-allyl)-anilide
O-4-chlorophenylsulfonylglycolic acid-(N-allyl)-anilide
O-butylsulfonylglycolic acid-(N-isopropyl)-anilide, m.p. 76° to 78°C
O-pentylsulfonylglycolic acid-(N-isopropyl)-anilide, m.p. 50° to 52°C
O-cyclohexylsulfonylglycolic acid-(N-isopropyl)-anilide, m.p. 110° to 112°C
O-benzylsulfonylglycolic acid-(N-isopropyl)-anilide, m.p. 107° to 108°C
O-isopropylsulfonylglycolic acid-(N-sec-butyl)-anilide, m.p. 55° to 56°C
O-butylsulfonylglycolic acid-(N-sec-butyl)-anilide, m.p. 44° to 46°C
O-pentylsulfonylglycolic acid-(N-butyn-1-yl-3)-anilide, m.p. 49° to 50°C
O-benzylsulfonylglycolic acid-(N-butyn-1-yl-3)-anilide, m.p. 65° to 66°C.

The corresponding O-sulfonyl-N-alkenyl- and O-sulfonyl-N-alkylglycolic acid anilides may be prepared from suitable O-sulfonyl-N-alkynylglycolic acid anilides by partial or complete hydrogenation of the carbon-carbon triple bond.

EXAMPLE 2

Preparation of O-methylsulfonylglycolic acid-(N-buten-1-yl-3)-anilide 1 part by weight of catalyst (0.7% by weight palladium on calcium carbonate, with added zinc) was added to a solution of 28.1 parts by weight of O-methylsulfonylglycolic acid-(N-butyn-1-yl-3)-anilide in 180 parts by weight of ethyl acetate, and hydrogenation carried out until 2,350 parts by volume of hydrogen had been absorbed at room temperature and 0.02 atmosphere gauge. The catalyst was then separated, the solution evaporated to dryness in vacuo and the residue recrystallized from ether; m.p.: 54° to 55°C.

Similarly, O-methylsulfonylglycolic acid-(N-sec-butyl)-anilide (m.p.: 68° to 70°C) may be obtained by complete hydrogenation employing a palladium on activated carbon (10%) catalyst.

The agents according to the invention may be used as solutions, emulsions, suspensions or dusts. The form of application depends entirely on the purpose for which the agents are being used; in any case it should ensure a fine distribution of the active ingredient.

For the preparation of solutions to be sprayed direct, hydrocarbons having boiling points higher than 150°C, e.g. tetrahydronaphthalene or alkylated naphthalenes, or organic liquids having boiling points higher than 150°C and having one or more than one functional group, e.g. the keto group, the ether group, the ester group or the amide group, this group or these groups being attached as substituent(s) to a hydrocarbon chain or being a component of a heterocyclic ring, may be used as spray liquids.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g., polyethylene oxide adducts. Concentrates which are suitable for dilution with water may be prepared from active ingredient, emulsifying or dispersing agent and possibly solvent. Oils or adhering agents may also be added.

Dusts may be prepared by mixing or grinding the active ingredients with a solid carrier, e.g., kieselguhr, talc, clay or fertilizers.

Granules may be prepared by blending with solid carriers.

EXAMPLE 3

Loamy sandy soil was filled into pots and sown with *Zea mays, Soja hispida, Gossypium hirsutum, Echinochloa crusgalli, Setaria spp., Poa trivialis, Lolium multiflorum* and *Sinapis arvensis*.

The soil was then treated with 2 kg per hectare of O-methylsulfonylglycolic acid-(N-butyn-1-yl-3)-anilide (I), 2 kg per hectare of O-methylsulfonylglycolic acid-(N-sec-butyl)-anilide (II) and, for comparison, with 2 kg per hectare of N-propargyl-α-chloroacetanilide (III) and 2 kg per hectare of N-butyn-(1)-yl-(3)-chloroacetic acid anilide (VII), each active ingredient being dispersed in 500 liters of water per hectare.

After 4 to 5 weeks it was observed that I and II had a stronger herbicidal action on the broadleaved and grassy weeds than III and VII, combined with the same good crop plant compatibility.

The results of this experiment are given below:

|  | I | II | III | VII |
|---|---|---|---|---|
| Zea mays | 0 | 0 | 0 | 0 |
| Soja hispida | 0 | 0 | 0 | 10 |
| Gossypium hirsutum | 0 | 0 | 0 | 0 |
| Echinochloa crus-galli | 100 | 100 | 70 | 95 |
| Setaria spp. | 100 | 95 | 70 | 85 |
| Poa trivialis | 100 | 75 | 40 | 65 |
| Lolium multiflorum | 95 | 75 | 40 | 70 |
| Sinapis arvensis | 75 | 40 | 20 | 20 |

0 = no damage
100 = complete destruction

The action of the following compounds corresponds to that of I and II in this experiment:

O-methylsulfonylglycolic acid-(N-isopropyl)-anilide
O-methylsulfonylglycolic acid-(N-isobutyl)-anilide.

EXAMPLE 4

The plants *Zea mays, Triticum aestivum, Echinochloa crusgalli, Setaria spp.*, and *Panicum spp.* were treated at a growth height of from 5 to 15 cm with 3 kg per hectare of each of the following active ingredients, each being dispersed in 500 liters of water per hectare:

O-methylsulfonylglycolic acid-(N-butyn-1-yl-3)-anilide (I);

O-methylsulfonylglycolic acid-(N-sec-butyl)-anilide (II);

and, for comparison,

N-propargyl-α-chloroacetanilide (III);
N-butyn-(1)-yl-(3)-α-chloroacetanilide (VII).

After 3 to 4 weeks it was ascertained that active ingredients I and II had a stronger herbicidal action on the broadleaved and grassy weeds than III and VII, combined with the same or superior crop plant compatibility.

The results of this experiment are given below:

|  | I | II | III | VII |
|---|---|---|---|---|
| Zea mays | 0 | 0 | 0 | 0 |
| Triticum aestivum | 0 | 0 | 10 | 30 |
| Echinochloa crus-galli | 95 | 80 | 65 | 70 |
| Setaria spp. | 80 | 70 | 55 | 50 |
| Panicum spp. | 85 | 75 | 60 | 50 |
| Matricaria chamomilla | 90 | 80 | 60 | 70 |

0 = no damage
100 = complete destruction

The action of the following compounds corresponds to that of I and II above:

O-methylsulfonylglycolic acid-(N-isopropyl)-anilide
O-methylsulfonylglycolic acid-(N-isobutyl)-anilide.

EXAMPLE 5

Loamy sandy soil was filled into pots and sown with Zea mays, Soja hispida, Gossypium hirsutum, Beta vulgaris, Echinochloa crus-galli, Setaria spp., Poa trivialis, Bromus tectorum and Alopecurus myosuroides.

The soil prepared in this manner was then treated with 2 kg per hectare of each of the following active ingredients, each being dispersed in 500 liters of water per hectare:

O-ethylsulfonylglycolic acid-(N-butyn-1-yl-3)-anilide (IV);
O-n-butylsulfonylglycolic acid-(N-butyn-1-yl-3)-anilide (V);

and, for comparison,

N-isopropyl-α-chloroacetanilide (VI);
N-butyn-(1)-yl-(3)-α-chloroacetanilide (VII).

After 4 to 5 weeks it was ascertained that active ingredients IV and V had a stronger herbicidal action than VI and VII, combined with the same or superior crop plant compatibility.

The results are given below:

|  | IV | V | VI | VII |
|---|---|---|---|---|
| Zea mays | 0 | 0 | 0 | 0 |
| Soja hispida | 0 | 0 | 0 | 10 |
| Gossypium hirsutum | 0 | 0 | 0 | 0 |
| Beta vulgaris | 0 | 0 | 0 | 10 |
| Echinochloa crus-galli | 100 | 100 | 70 | 95 |
| Setaria spp. | 100 | 100 | 70 | 85 |
| Poa trivialis | 95 | 95 | 40 | 65 |
| Bromus tectorum | 95 | 95 | 40 | 45 |
| Alopecurus myosuroides | 100 | 70 | 50 | 60 |

0 = no damage
100 = complete destruction.

EXAMPLE 6

The plants Zea mays, Gossypium hirsutum, Beta vulgaris, Echinochloa crus-galli, Poa annua, Panicum spp. and Avena fatua were treated at a growth height of from 3 to 15 cm with 4 kg per hectare of each of the following active ingredients, each being dispersed in 500 liters of water per hectare:

O-ethylsulfonylglycolic acid-(N-butyn-1-yl-3)-anilide (IV);
O-n-butylsulfonylglycolic acid-(N-butyn-1-yl-3)-anilide (V);

and, for comparison,

N-isopropyl-α-chloroacetanilide (VI);
N-butyn-(1)-yl-(3)-α-chloroacetanilide (VII).

After 3 to 4 weeks it was ascertained that active ingredients IV and V had superior crop plant compatibility and a stronger herbicidal action than compounds VI and VII.

The results of the experiment are given below:

|  | IV | V | VI | VII |
|---|---|---|---|---|
| Zea mays | 0 | 0 | 5 | 10 |
| Gossypium hirsutum | 0 | 0 | 25 | 25 |
| Beta vulgaris | 10 | 0 | 20 | 30 |
| Echinochloa crus-galli | 90 | 85 | 70 | 80 |
| Poa annua | 90 | 90 | 30 | 60 |
| Panicum spp. | 95 | 90 | 65 | 70 |
| Avena fatua | 80 | 80 | 40 | 45 |

0 = no damage
100 = complete destruction

EXAMPLE 7

90 parts by weight of compound I is mixed with 10 parts by weight of N-methyl-α-pyrrolidone. A mixture is obtained which is suitable for application in the form of very fine drops.

EXAMPLE 8

20 parts by weight of compound II is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of compound IV is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous disperison is obtained containing 0.02% by weight of the active ingredient.

EXAMPLE 10

20 parts by weight of compound V is dissolved in a mixture consisting of 25 parts by weight of cyclohexanol, 65 parts by weight of a mineral oil fraction having a boiling point between 210° and 280°C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 11

20 parts by weight of compound I is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 12

3 parts by weight of compound II is intimately mixed with 97 parts by weight of particulate kaolin. A dust is obtained containing 3% by weight of the active ingredient.

EXAMPLE 13

30 parts by weight of compound IV is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 14

In the greenhouse, loamy sandy soil was filled into pots and sown with Zea mays, Gossypium hirsutum, Glycine hispida, Beta vulgaris, Brassica oleracea, Echinochloa crus-galli, Setaria faberii, Alopecurus myosuroides and Eleusine indica. The soil prepared in this manner was then treated with 1 and 2 kg per hectare of each of the following active ingredients, each being emulsified in 500 liters of water per hectare:

I. O-methylsulfonylglycolic acid-[N-butyn-(1)-yl-(3)]-anilide;
II. O-n-butylsulfonylglycolic acid-[N-butyn-(1)-yl-(3)]-anilide;
III. O-phenylsulfonylglycolic acid-[N-butyn-(1)-yl-(3)]-anilide;
IV. O-p-methylphenylsulfonylglycolic acid-[N-butyn-(1)-yl-(3)]-anilide;
V. O-methylsulfonylglycolic acid-(N-methyl)-anilide.

After 4 to 5 weeks it was ascertained that active ingredients I to IV had a stronger herbicidal action than comparative agent V, combined with the same excellent crop plant compatibility.

The results of this experiment are given below:

| kg/ha | I | | II | | III | |
|---|---|---|---|---|---|---|
| | 1 | 2 | 1 | 2 | 1 | 2 |
| Zea mays | 0 | 0 | 0 | 0 | 0 | 0 |
| Gossypium hirsutum | 0 | 0 | 0 | 0 | 0 | 0 |
| Soja hispida | 0 | 0 | 0 | 0 | 0 | 0 |
| Beta vulgaris | 0 | 0 | 0 | 0 | 0 | 0 |
| Brassica oleracea | 0 | 0 | 0 | 0 | 0 | 0 |
| Echinochloa crus-galli | 90–100 | 100 | 100 | 100 | 90 | 90–100 |
| Setaria Faberii | 90–100 | 100 | 100 | 90 | 90–100 | |
| Alopecurus myosuroides | 80 | 90 | 90 | 100 | 60–70 | 80 |
| Eleusine indica | 90–100 | 100 | 90–100 | 100 | 90 | 90–100 |

| kg/ha | IV | | V | |
|---|---|---|---|---|
| | 1 | 2 | 1 | 2 |
| Zea mays | 0 | 0 | 0 | 0 |
| Gossypium hirsutum | 0 | 0 | 0 | 0 |
| Soja hispida | 0 | 0 | 0 | 0 |
| Beta vulgaris | 0 | 0 | 0 | 0 |
| Brassica oleracea | 0 | 0 | 0 | 0 |
| Echinochloa crus-galli | 90–100 | 100 | 70–80 | 90 |
| Setaria faberii | 90–100 | 100 | 70 | 80–90 |
| Alopecurus myosuroides | 80–90 | 90–100 | 50–60 | 70–80 |
| Eleusine indica | 90–100 | 100 | 70–80 | 80–90 |

0 = no damage
100 = complete destruction

EXAMPLE 15

In the greenhouse, the plants Zea mays, Glycine hispida, Gossypium hirsutum, Beta vulgaris, Oryza sativa, Triticum aestivum, Hordeum vulgare, Eleusine indica, Echinochloa crus-galli, Setaria faberii, Panicum virgatum, Digitaria sanguinalis, Alopecurus myosuroides and Poa annua were treated at a growth height of the crop plants of 7 to 15 cm and of the broadleaved and grassy weeds of 2 to 10 cm with 1 kg per hectare of each of the following active ingredients, each being emulsified in 500 liters of water per hectare:

I. O-methylsufonylglycolic acid-[N-butyn-(1)-yl-(3)]-anilide
II. O-n-butylsulfonylglycolic acid-[N-butyn-(1)-yl-(3)]-anilide
III. O-methylsulfonylglycolic acid-(N-methyl)-anilide.

After 3 to 4 weeks it was observed that I and II had a better herbicidal action than comparative agent III, combined with the same good crop plant compatibility.

The results of this experiment are given below:

| | I | II | III |
|---|---|---|---|
| Zea mays | 0–10 | 0–10 | 10 |
| Glycine hispida | 0 | 0 | 5 |
| Gossypium hirsutum | 0 | 0 | 0 |
| Beta vulgaris | 0 | 0 | 0 |
| Oryza sativa | 0–10 | 0–10 | 0–10 |
| Triticum aestivum | 0–10 | 0–10 | 0–10 |
| Hordeum vulgare | 0–10 | 0–10 | 0–10 |
| Eleusine indica | 90–100 | 90–100 | 60–70 |
| Echinochloa crus-galli | 90–100 | 100 | 40–50 |
| Setaria faberii | 90–100 | 100 | 60 |
| Panicum virgatum | 90–100 | 100 | 60 |
| Digitaria sanguinalis | 90–100 | 90–100 | 60–70 |
| Alopecurus myosuroides | 90–100 | 100 | 60–70 |

| | I | II | III |
|---|---|---|---|
| *Poa annua* | 100 | 100 | 70–80 |

0 = no damage
100 = complete destruction

The action of the following compounds corresponds to that of I and II in this example:

O-phenylsulfonylglycolic acid-[N-butyn-(1)-yl-(3)]-anilide

O-p-methylphenylsulfonylglycolic acid-[N-butyn-(1)-yl-(3)]-anilide.

We claim:
1. O-methylsulfonylglycolic acid-(N-isopropyl)-anilide.
2. O-methylsulfonylglycolic acid-(N-isobutyl)-anilide.
3. O-methylsulfonylglycolic acid-(N-sec-butyl)-anilide.
4. O-ethylsulfonyglycolic acid-(N-isopropyl)-anilide.
5. O-n-propylsulfonylglycolic acid-(N-isopropyl)-anilide.
6. O-isopropylsulfonylglycolic acid-(N-isopropyl)-anilide.

* * * * *